United States Patent
Shen et al.

(10) Patent No.: US 6,534,637 B2
(45) Date of Patent: Mar. 18, 2003

(54) SYNTHESIS OF CHLOROPHENOL RED GLUCURONIC ACID

(75) Inventors: Gene G. Y. Shen, Diamond Bar, CA (US); Chan S. Oh, Chino Hills, CA (US); Stephanie D. Yancey, La Habra, CA (US); Craig W. Adams, Yorba Linda, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/781,885

(22) Filed: Feb. 12, 2001

(65) Prior Publication Data

US 2002/0115128 A1 Aug. 22, 2002

(51) Int. Cl.[7] .................. C12Q 1/54; C07H 15/203; C07H 15/20
(52) U.S. Cl. ............... 536/18.2; 435/4; 435/6; 435/14; 514/25; 536/4.1; 536/17.5; 536/17.6; 536/17.9; 536/18.1; 536/94; 536/95
(58) Field of Search .......... 435/4, 6, 14; 514/25; 536/4.1, 17.5, 17.6, 17.9, 18.1, 18.2, 94, 95

(56) References Cited

U.S. PATENT DOCUMENTS

| | | | |
|---|---|---|---|
| 4,226,978 A | 10/1980 | Boguslaski et al. | 536/4 |
| 4,351,823 A | 9/1982 | Rubin | 424/9 |
| 4,424,348 A | 1/1984 | Rubin | 536/17.9 |
| 4,668,622 A | 5/1987 | Kuhr et al. | 435/14 |

(List continued on next page.)

FOREIGN PATENT DOCUMENTS

| | | | |
|---|---|---|---|
| EP | 0 025 467 A1 | 3/1925 | C12Q/1/04 |
| EP | 0 146 866 A2 | 5/1987 | C07H/15/203 |
| JP | 2000270894 A | 10/2000 | C12Q/1/34 |

OTHER PUBLICATIONS

"Synthesis of 4–Methylumbelliferyl 1,2–cis–Glycosides," Marie–Christine Courtin–Duchateau et al., *Carbohydrate Research*, 65 (1978), pp. 23–33.

(List continued on next page.)

*Primary Examiner*—Peter O'Sullivan
(74) *Attorney, Agent, or Firm*—William H. May; D. David Hill; Hogan & Hartson LLP (57) ABSTRACT

This invention provides β-D-Glucuronidase substrates of the formula:

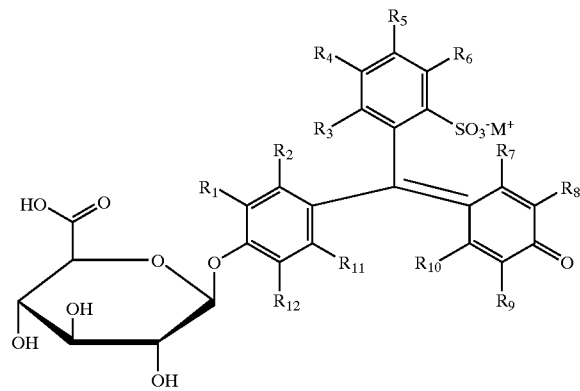

wherein $R_1$, $R_2$, and $R_7$–$R_{12}$ are independently selected from the group consisting of:
  hydrogen, fluorine, chlorine, bromine, iodine, alkyl, hydroxyl, alkoxy, carboxyl and nitro groups;

$R_3$–$R_6$ are independently selected from the group consisting of hydrogen, fluorine, chlorine, bromine, iodine, nitro and amino; and $M^+$ is selected from the group consisting of: proton, lithium, sodium, potassium, magnesium, calcium, barium, and ammonium ion.

24 Claims, 3 Drawing Sheets

U.S. PATENT DOCUMENTS

| | | | | |
|---|---|---|---|---|
| 5,068,180 A | * | 11/1991 | Hwang et al. | 435/7.92 |
| 5,208,148 A | | 5/1993 | Haugland et al. | 435/14 |
| 5,242,805 A | | 9/1993 | Naleway et al. | 435/18 |
| 5,272,260 A | | 12/1993 | Pope et al. | 536/18.1 |
| 5,358,854 A | * | 10/1994 | Ferguson | 435/14 |
| 5,599,670 A | | 2/1997 | Jefferson | 435/6 |
| 5,633,144 A | | 5/1997 | Bitton et al. | 435/38 |
| 5,849,515 A | | 12/1998 | Grant | 435/34 |
| 6,063,588 A | | 5/2000 | Lamster | 435/18 |

OTHER PUBLICATIONS

"β–Glucuronidase from *Escherichia coli* as a gene–fusion marker," Richard A. Jefferson et al., *Proc. Natl. Acad. Sci. USA*, vol. 83, pp. 8447–8451, Nov. 1986, Biochemistry.

"Heparanases and Tumor Matastatis," Motowo Nakajima, Tatsuro Irimura and Garth L. Nicolson, *Journal of Celular Biochemistry*, 36:157–167 (1988), *Tumor Progression and Metastasis*, 49–59.

Wu et al; "Sensitive Method for the Quantification of beta–glucuronidase Activity in Human Urine using Capillary Electrophoresis with Fluorescence Detection"; *Journal of Chromatography B: Biomedical Sciences & Applications, Elsevier Science*. vol. 708, No. 1–2; pp. 61–66, (Apr. 24, 1998).

Jhenjun, D. et al; "Fluorescent Molecular Probes I. The Synthesis and Biological Properties of an ELF (☐–glucuronidase Substrate That Yields Fluorescent Precipitates at the Enzymatica Activity Sites"; *Tetrahedron*, vol. 53, No. 21, pp. 7159–7164, 1977.

* cited by examiner

SYNTHESIS OF CHLOROPHENOL RED GLUCURONIC ACID

BACKGROUND OF THE INVENTION

1. Area of the Art

This invention relates to β-D-Glucuronidase substrates, methods of their synthesis and methods of their use.

2. Description of the Prior Art

The activity of β-D-Glucuronidase (GUD) is extremely common in tissues of all vertebrates and many mollusks (Levvy, G. A. and Conchie, J., 1966, NY. p. 301). GUD is a key enzyme in the breakdown of proteoglycans constituting extracellular matrix and endothelial basal membrane. Yet, excessively high activity of the enzyme has been associated with certain tumors and bacterial infections (U.S. Pat. No. 4,351,823). For example, a metastatic potential of tumor cells has been linked with their GUD activity (M. Nakajima et al., J. Cellular Biochem. 36: 157–167, 1988). Similarly, elevated levels of CUD in gingival crevicular fluid and in saliva were indicative of existing periodontal disease and correlated with the likelihood of future disease progression (U.S. Pat. No. 6,063,588). In addition to its physiological importance, due to its smaller size and greater stability, GUD is a popular alternative to β-galactosidase for use as an analyte indicator in enzyme assays and immunoassays. Consequently, the determination of the activity of GUD is of increasing importance in clinical chemistry, diagnostic assays, molecular biology, and certain environmental applications.

Conventionally, the determination of GUD involves the use of insoluble chromogenic substrates. For example, insoluble substrates 5-bromo-4-chloro-3-indolyl-β-D-glucuronide (X-gluc) and indoxyl-β-D-glucuronide were successfully used for the detection of *E. coli* on a solid media (U.S. Pat. No. 5,358,854). Similarly, in another study, *E. coli* colonies were identified by the formation of a black precipitate on chromogenic substrate 8-hydroxyquinoline glucuronide in combination with X-glucuronide (European Patent Application Publication 0025467). Although insoluble chromogenic GUD substrates provide a convenient and fast way to detect *E. coli* colonies based on their GUD activity, such insoluble substrates cannot be used in homogenous enzymatic assays. Quantitative enzyme assays are typically conducted in liquid extracts and rely on absorption or fluorescence detection methods. Consequently, soluble GUD substrates are required for such assays.

The detection of fluorescent molecules offers a very high signal-to-noise ratio because the incident excitation light does not impinge on the detection apparatus, and has a spectrum distinct and separable from that of the emission. For example, 3-carboxy-umbelliferyl β-D-glucuronide, fluorescein glucuronide, resorufin glucuronide, methylumbelliferyl glucuronide were found to be useful substrates for fluorogenic assays of GUD activity (U.S. Pat. Nos. 4,226,978 and 5,599,670). However, because fluorescence emission is dependent on the intensity and wavelength of the excitation light, any factors in an assay mixture which affect the available excitation intensity or wavelength will correspondingly affect the apparent fluorescence output. Therefore, intrinsic background fluorescence common to biological samples is a serious problem limiting assay sensitivity. In order to minimize background fluorescence, the fluorescent compounds may be extracted prior to the sample analysis. However, such an approach makes the assay more time-consuming and complicated. Additionally, fluorometrical methods require a relatively expensive equipment.

Spectrophotometric assays, on the other hand, are very straightforward and moderately sensitive (Jefferson et al., 1986, Proc. Natl. Acad. Sci. USA 86:8447–8451). Because of the remarkable stability of GUD, one can enhance the sensitivity of spectrophotometric assays quite significantly by carrying out assays on a longer time scale to provide linear, reproducible results. Also, spectrophotometric assays are inexpensive, easy to automate, and easy to quantitate without sophisticated instrumentation (U.S. Pat. No. 5,599,670).

The currently preferred soluble substrate for the spectrophotometric measurement of GUD activity is p-nitrophenyl-β-D-glucuronide. This substrate, when cleaved by GUD, releases the chromophore p-nitrophenol. At a pH greater than its $pK_a$ (around 7.15), the ionized chromophore absorbs light at 400–420 nm ($\lambda_{max}$ of 415 nm and $\epsilon=14,000$), giving a yellow color. Unfortunately, often biological sample matrix is rich with compounds that absorb at the maximum wavelength of p-nitrophenol and, therefore, interfere with GUD detection.

Alternatively, phenolphthalein-β-D-glucuronide may be used as a chromogenic substrate for GUD. The cleaved substrate by GUD phenolphthalein produces a purple color ($\lambda_{max}=550$ nm and $\epsilon=3000$) under alkaline conditions. This substrate is not in wide use now, due to its expense and very low extinction coefficient (U.S. Pat. No. 5,599,670).

SUMMARY OF THE INVENTION

Due to the above-discussed shortcomings of the related art, there is a need for new soluble GUD chromogenic substrates that allow fast, sensitive, and simple determination of GUD in a broad range of samples. Accordingly, it is an object of the present invention to provide such substrates, methods of their synthesis and methods of their use.

These and other objects and advantages are achieved in a β-D-Glucuronidase (GUD) substrate of the following formula (IV):

IV

In this formula, $R_1$, $R_2$, and $R_7$–$R_2$ are independently selected from the group consisting of: hydrogen, fluorine, chlorine, bromine, iodine, alkyl, hydroxyl, alkoxy, carboxyl and nitro groups; $R_3$–$R_6$ are independently selected from the group consisting of hydrogen, fluorine, chlorine, bromine, iodine, nitro and amino; and $M^+$ is selected from the group consisting of: proton, lithium, sodium, potassium, magnesium, calcium, barium, and ammonium ion. In one embodiment, $R_1$–$R_8$, $R_{10}$, and $R_{11}$ are hydrogen atoms, $M^+$ is sodium, and $R_9$ and $R_{12}$ are chlorines.

Another aspect of the present invention provides a method of synthesizing a GUD substrate. The method comprises the steps of:

(a) forming a conjugate (III), having a formula:

(III)

and (b) replacing Ac and Me groups with hydrogens.

In the formula (III), $R_1$, $R_2$, and $R_7$–$R_{12}$ are independently selected from the group consisting of: hydrogen, fluorine, chlorine, bromine, iodine, alkyl, hydroxyl, alkoxy, carboxyl and nitro groups; $R_3$–$R_6$ are independently selected from the group consisting of hydrogen, fluorine, chlorine, bromine, iodine, nitro and amino; $M^+$ is selected from the group consisting of: proton, lithium, sodium, potassium, magnesium, calcium, barium, and ammonium ion; Ac is an acetyl group; and Me is a methyl group.

A further aspect of the present invention provides a method for determining the presence of GUD activity in a sample. The method comprises the steps of:

(a) contacting the sample with a GUD substrate (IV) of the present invention under a condition that allows the release of phenolsulphonphthalein;

(b) detecting phenolsulphonphthalein in the sample; and (c) correlating the presence of phenolsulphonphthalein in the sample to a presence of GUD.

The detection step may be carried out by measuring the light absorption of the sample within a wavelength range that includes a wavelength of maximum absorption by phenolsulphonphthalein. In one embodiment of the present invention, the intensity of the measured light absorption is correlated to the activity of GUD in the test sample. In another embodiment, the intensity of the measured light absorption is correlated to the concentration of GUD in the test sample. The method may be used for both qualitative and quantitative analysis of GUD in samples.

The substrate of the present invention is well-suited for use with any detection equipment. In one embodiment, a colorimetric detector found on the CX®, SX® and LX® SYNCHRON® systems (Beckman Coulter, Calif.) is used to detect phenolsulphonphthalein released from the substrate by GUD.

Another aspect of the present invention provides a test kit for determining the presence of GUD in a test sample. The test kit comprises GUD substrate (IV) of the present invention.

The most immediate application of the substrate and kit of the present invention includes a development of calorimetric assays for biochemical and clinical markers based on measured GUD activity in a sample. For example, Prostate Specific Antigen, myocardial infarction indicators, e.g. Creatine Kinase-MB and Troponin I, and traumatic muscle injury indicators, e.g. myoglobin, can be accurately detected using GUD substrate of this invention. Additionally, the detection and quantitative analysis of GUD activity in biological samples may allow diagnosis of certain bacterial infections.

Alternatively, recombinant DNA comprising a nucleic acid sequence encoding GUD, together with an appropriate controller sequence, may be introduced into a host cell or organism using any method known in the art, including transfection, transformation, infection, or microinjection to form a reporter gene system. In this application, the novel substrate of the present invention will be used to measure GUD activity and to correlate it to the activity of the controller element.

The present invention provides both economic and technical advantages over the use of other GUD substrates. The instant soluble GUD substrate provides highly sensitive, fast, and simple determination of GUD in a broad range of samples. Due to its high sensitivity, smaller quantities of the GUD substrate may be used.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope.

BRIEF DESCRIPTION OF THE DRAWINGS

DETAILED DESCRIPTION OF THE INVENTION

The present invention provides a novel soluble β-D-Glucuronidase (GUD) substrate. The GUD substrate of the present invention has the following formula (IV):

(IV)

In the formula (IV), $R_1$, $R_2$, and $R_7$–$R_{12}$ are independently selected from the group consisting of: hydrogen, fluorine, chlorine, bromine, iodine, alkyl, hydroxyl, alkoxy, carboxyl and nitro groups;

$R_3$–R6 are independently selected from the group consisting of hydrogen, fluorine, chlorine, bromine, iodine, nitro and amino; and $M^+$ is selected from the group consisting of: proton, lithium, sodium, potassium, magnesium, calcium, barium, and ammonium ion.

In one embodiment, alkyl and alkoxy groups have 1 to 5 carbon atoms. In another embodiment, at least one of the groups $R_1$ and $R_{12}$ is fluorine, chlorine, or bromine. In a preferred embodiment, $R_1$–$R_8$, $R_{10}$, and $R_{11}$ are hydrogen atoms, $M^+$ is sodium, $R_9$ and $R_{12}$ are chlorines, and the GUD substrate has the following structure (IVA):

(IVA)

The GUD substrates (IV) and (IVA) of the present invention have a number of unexpected advantages over the conventional chromogenic GUDs. The instant GUD substrates are highly soluble and can be easily employed in liquid homogeneous assay formats. Additionally, the sensitivity of GUD assay increases significantly when conventional substrates are replaced with the substrates of the present invention.

Figure 1:
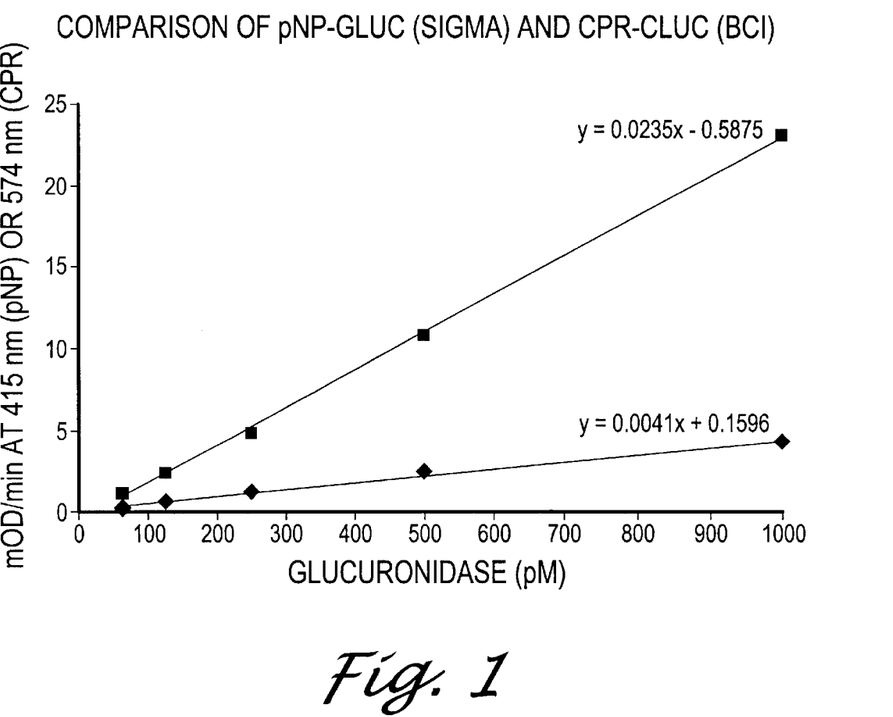
FIG. 1 shows rates of reaction between GUD and chlorophenol red glucuronide (top graph) and between GUD and p-nitrophenol glucuronide (bottom graph) for a range of GUD concentrations.

When a substrate of the present invention is digested by GUD, a phenolsulphonphthaleinyl, such as chlorophenol red, is released into the sample. Phenolsulphonphthaleinyls have high extinction coefficients and usually adsorb light in the range from 550 nm to 600 nm, where an interference from the matrix is minimal. Consequently, intensity of the optical signals and sensitivity of GUD assay are substantially higher with the substrates of the present invention in comparison with the conventional substrates. For example, as shown in FIG. 1, when identical amounts of GUD are added to a substrate of the present invention, chlorophenol red glucuronide, (top graph) and to nitro-phenol glucuronide (bottom graph), the instant substrate generates a signal, which is about six-fold more intensive than the signal generated by nitro-phenol glucuronide.

Another aspect of the present invention provides a method of synthesizing a GUD substrate. The method comprises the steps of:

(a) forming a conjugate (III) having a formula:

(III)

and
(b) replacing Ac and Me groups with hydrogens.

In the formula (III), $R_1$, $R_2$, and $R_7$–$R_{12}$ are independently selected from the group consisting of: hydrogen, fluorine, chlorine, bromine, iodine, alkyl, hydroxyl, alkoxy, carboxyl and nitro groups; $R_3$–$R_6$ are independently selected from the group consisting of hydrogen, fluorine, chlorine, bromine, iodine, nitro and amino; $M^+$ is selected from the group consisting of: proton, lithium, sodium, potassium, magnesium, calcium, barium, and ammonium ion; Ac is an acetyl group; and Me is a methyl group.

Ac and Me groups may be replaced with hydrogens by any method that are known in the art as long as it leads to the formation of a stable compound (IV). In one embodiment, a mixture of sodium methoxide and methanol is added to a solution of the conjugate (III) in methanol at room temperature under nitrogen. The reaction is stirred for 20 minutes and solvent is evaporated to dryness. A diluted (0.1N) sulfuric acid is added to the precipitate and stirred overnight. The solution is then neutralized with 0.1 N NaOH and dried to obtain compound (IV).

The conjugate (III) may be obtained by any method. In one embodiment shown in FIG. 1, the conjugate (III) is obtained by:

(a) mixing bromo-2,3,4-tri-O-acetyl-α-D-glucuronic acid methyl ester and a phenolsulphonphthalein to form a reaction mixture; and (b) maintaining the reaction mixture under conditions that allow the formation of the conjugate (III).

Any reaction conditions are acceptable as long as they are sufficient to allow the stable formation of the conjugate (III). For example, a solution of potassium carbonate in N,N-dimethylformamide may be added to the reaction mixture and stirred at room temperature to form the conjugate (III). The phenolsulphonphthaleins are either known, commercially available substances or can be prepared by known processes. For example, the phenolsulphonphthaleins may be synthesized from a phenol and an o-sulphonbenzoic acid or, starting from known sulphonphthaleins, by subsequent derivatization, i.e., by halogenation or nitration (U.S. Pat. No. 4,668,622). Bromo-2,3,4-tri-O-acetyl-α-D-glucuronic acid methyl esters employed as starting materials are also known compounds. They are described, for example, in Japanese Patent No. 2000-270894.

Figure 2:
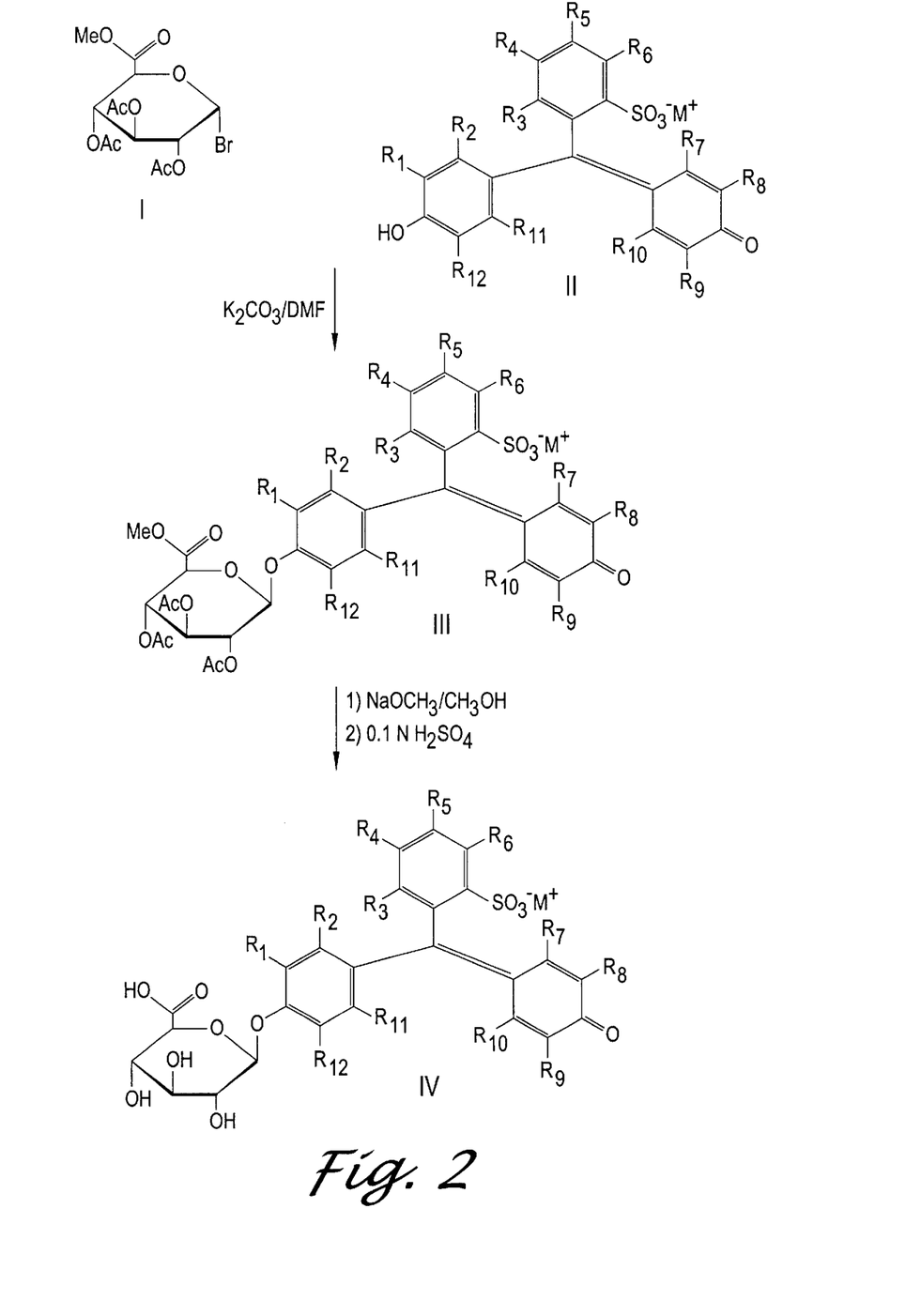
FIG. 2 shows a general reaction scheme for the synthesis of phenolsulphonphthaleinyl-β-D- Glucuronide.
Figure 3:
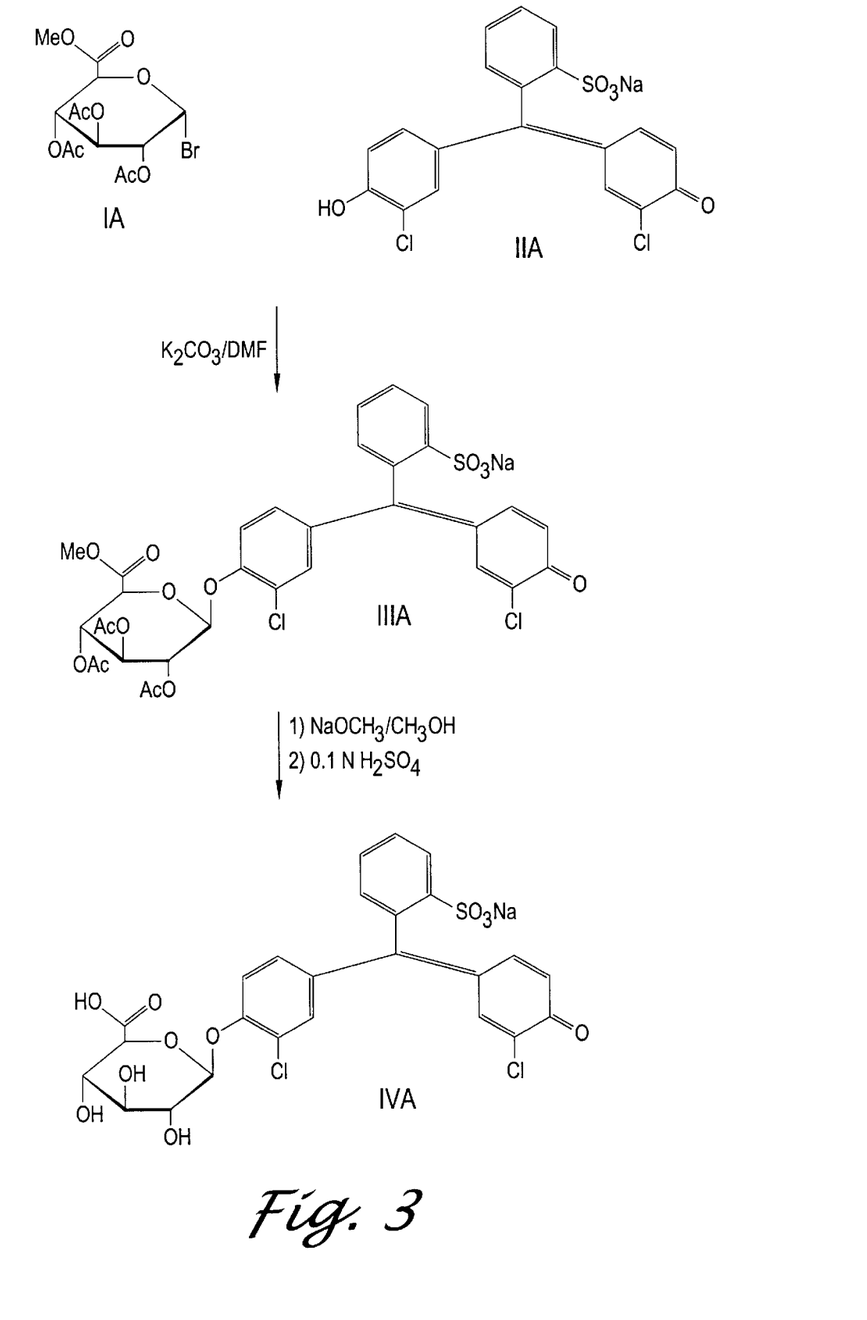
FIG. 3 shows a reaction scheme for the synthesis of chlorophenol red glucuronic acid.

In a preferred embodiment shown in FIG. 2, the conjugate has a structure (IIIA), wherein $R_1$–$R_8$, $R_{10}$, and $R_{11}$ are hydrogen atoms, $M^+$ is sodium, $R_9$ and $R_{12}$ are chlorines.

The conjugate (IIIA) is obtained by stirring at room temperature a solution of bromo-2,3,4-tri-O-acetyl-α-D-glucuronic acid methyl ester (IA), chlorophenol red (IIA), and potassium carbonate in N,N-dimethylformamide. In one embodiment, the crude residual product (IIIA) was subjected to column chromatography on silica gels to afford a purified solid product (IIIA).

The preferred reaction schemes disclosed in FIGS. 1 and 2 provide much gentler reaction conditions as compared to a reaction scheme used in the synthesis of phenolsulphonphthaleinyl-β-D-galactosides described in U.S. Pat. No. 4,668,622. For example, in the present invention, both steps of the synthesis are conducted at room temperature for a cumulative of about 25 hours. The intermediate is purified by column chromatography on silica gel. In the U.S. Pat. No. 4,668,622, on the other hand, the reaction mixture is first warmed to 60°, then boiled for 12 hours, and then left to stand for another 8 hours at ambient temperature. After that, additional chemicals are added and the reaction mixture is cooled to 0°–5° and mixed for an additional 2 hours. Also, the intermediates are isolated using organic extraction methods.

The instant method, therefore, provides substantial technical and economic advantages over the method disclosed in the U.S. Pat. No. 4,668,622. The instant method is simpler, uses fewer chemicals, and does not require any heating or cooling of the reaction mixture, thus providing energy and labor savings.

Another aspect of the present invention provides a method for determining the presence of GUD activity in a sample. The method comprises the steps of:

(a) contacting the sample with a GUD substrate (IV) of the present invention under a condition that allows the release of phenolsulphonphthalein;

(b) detecting phenolsulphonphthalein in the sample; and (c) correlating the presence of phenolsulphonphthalein in the sample to a presence of GUD.

The contacting step may be carried out under any conditions as long as they allow enzymatic split of the substrate (IV) with a release of phenolsulphonphthalein. In one embodiment, the sample and the substrate are mixed in a sodium phosphate buffer (pH=7.0) and reacted at room temperature. Other reaction conditions may be used and will be easily selected by those skilled in the art based on the instant disclosure.

The detection step may be carried out by any qualitative or quantitative method that allows the detection of an optical signal produced by the released phenolsulphonphthalein. Such methods include, but are not limited to spectroscopy and colorimetry. In one embodiment, light absorption of the sample is measured. The optical measurements are conducted within a wavelength range that includes a wavelength of maximum absorption by phenolsulphonphthalein. The measured signal may be correlated to the activity or concentration of GUD in the test sample. Methods of such correlation are well-known in the art and will not be repeated here.

In a preferred embodiment, the GUD substrate is chlorophenol red β-D-glucuronic acid (IVA). When contacted with a sample containing GUD, the substrate (IVA) releases chlorophenol red. Chlorophenol red has a violet color and has maximum adsorption at about 575 nm and has a high extinction coefficient. A high extinction coefficient and maximum adsorption are outside of the matrix interference range and, thus, make the instant test system much more sensitive than those previously known. Similar properties of other phenolsulphonphthalein substrates of the present invention make GUD detection methods disclosed herein advantageously sensitive.

Due to their high sensitivity, the disclosed methods allow the accurate determination of GUD activity in smaller and/or more diluted samples and in shorter time period.

Another aspect of the present invention provides a kit for determining the presence of GUD in a test sample. The test kit comprises compound (IV), preferably compound (IVA). Additionally, the test kit may contain an appropriate buffer system, as well as additional materials conventionally used for such diagnostic tests. For example, the test kit may include wetting agents and stabilizers. The compound (IV) may be provided in the form of a solution, a powder, or a reagent tablet. Alternatively, compound (IV) may be applied to an absorbent carrier. Methods of manufacturing reagents in desirable formats are well-known in the art and will not be discussed here.

The liquid samples to be tested may be a naturally-occurring or artificially-formed liquid suspected of containing GUD, and usually is a biological fluid or a liquid resulting from a dilution or other treatment thereof Biological fluids which may be assayed following the present method include serum, plasma, urine, saliva, and amniotic, cerebral, and spinal fluids. Other materials, such as solid matter, for example, tissue or gases, may be assayed by reducing them to a liquid form such as by dissolution of the solid or gas in a liquid or by liquid extraction of the solid.

The foregoing examples are meant to illustrate, but not to limit, the scope of the invention. Indeed, those of ordinary skill in the art can readily envision and produce further embodiments, based on the teachings herein, without undue experimentation.

EXAMPLE 1

Preparation of Chlorophenol Red 2,3,4-tri-O-Acetyl-β-D-glucuronic Acid Methyl Ester (IIIA)

As shown in FIG. 2, a solution of bromo-2,3,4-tri-O-acetyl-α-D-glucuronic acid methyl ester (IA) (1, 8.92 g, 22.4 mmol), chlorophenol red (IIA) (2, 7.5 g, 16.84 mmol), potassium carbonate (3.10 g, 22.4 mmol) in N,N-dimethylformamide (50 mL) was stirred at room temperature under nitrogen for 16 hours. The solid was filtered off and the filtrate was concentrated at reduced pressure to dryness. The crude residual product was subjected to column chromatography (silica gel). The product was eluted with gradient solvents (0% to 10% $CH_3OH/CH_2Cl_2$). The product fractions ($R_f$=0.6 on TLC plate, 4:1 $CH_2Cl_2:CH_3OH$) were combined and concentrated under reduced pressure to dryness to afford the solid product (IIIA) (2.93 g, 23%).

EXAMPLE 2

Preparation of Chlorophenol Red β-D-Glucuronic Acid (IVA)

As shown in FIG. 2, a 25% solution of $NaOCH_3/CH_3OH$ (342 μL, 1.5 mmol) was added to a solution of chlorophenol red 2,3,4-tri-O-acetyl-β-D-glucuronic acid methyl ester (IIIA) (200 mg, 0.26 mmol) in anhydrous methanol (10 mL) at. room temperature under nitrogen. The reaction was stirred for 20 minutes. The solvent was evaporated to dryness. A diluted $H_2SO_4$ (0.1 N, 3 mL) was added to the dried product and the solution was stirred at ambient temperature overnight. The solution was neutralized with 0.1 N NaOH and the solvent was evaporated to form a solid product. The product was purified by column chromatography (silica gel) eluted with gradient solvents (0% to 50% $CH_3OH/CH_2Cl_2$,). The product fractions ($R_f$=0.24 on TLC plate, 1:1 $CH_2Cl_2:CH_3OH$) were combined and concentrated under reduced pressure to dryness to afford the solid product (IVA) (8.3 mg, 5.1%).

EXAMPLE 3

Enzyme Assay

The suitability of the chlorophenol red β-D-glucuronic acid substrate (IVA) for detecting β-glucuronidase in a sample was tested following the procedure of Jefferson et al., *PNAS* (1986) Vol. 83, 8447–8451. The solid product (IVA) was dissolved in water to a final concentration of approximately 100 mM (red-orange product). An aliquot was added to 50 μM of purified β-glucuronidase (Sigma G-7896) in 50 MM sodium phosphate buffer, pH 7.0, 10 mM β-mercaptoethanol and 0.1% Triton X-100. The appearance of a violet product with the absorbance maximum at 575 nm indicated that the substrate (IVA) was suitable for the detection of β-glucuronidase in a sample.

EXAMPLE 4

Sensitivity of GUD Assay

*E. coli* α-D-Glucuronidase (Sigma, G7896) was diluted in PBS buffer containing 10 mM DTT and 0.1% Triton X-100 and either substrate p-nitrophenol glucuronide (Sigma N1627) or phenolsulphonphthaleinyl (or chlorophenol red) glucuronide of the present invention. The final concentration of each substrate was 1 mM. The final concentration of GUD was 60 pM, 125 pM, 250 pM, 500 pM, or 1000 pM. Readings of Optical Density (OD) were measured at 415 nm for assay with p-nitrophenol glucuronide and at 574 nm for assay with chlorophenol red glucuronide. OD measurements were conducted over 30 minutes at 37° C. in a Beckman DU70 spectrophotometer and the reaction rates were determined in mOD/min. Rates for the phenolsulphonphthaleinyl glucuronide were 5.76-fold higher than the nitrophenol-glucuronide substrate. Therefore, the sensitivity of the GUD assay utilizing a substrate of the present invention as compared to the sensitivity of GUD assay with a conventional substrate.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A β-D-Glucuronidase (GUD) substrate of the formula:

wherein $R_1$, $R_2$, and $R_7$–$R_{12}$ are independently selected from the group consisting of:
hydrogen, fluorine, chlorine, bromine, iodine, alkyl, hydroxyl, alkoxy, carboxyl and nitro groups;

$R_3$–$R_6$ are independently selected from the group consisting of hydrogen, fluorine, chlorine, bromine, iodine, nitro and amino; and $M^+$ is selected from the group consisting of: proton, lithium, sodium, potassium, magnesium, calcium, barium, and ammonium ion.

2. The GUD substrate of claim 1, wherein $M^+$ is sodium.

3. The GUD substrate of claim 1, wherein the alkyl has 1 to 5 carbon atoms.

4. The GUD substrate of claim 1, wherein the alkoxy has 1 to 5 carbon atoms.

5. The GUD substrate of claim 1, wherein at least one of $R_1$ to $R_{12}$ is fluorine, chlorine or bromine.

6. The GUD substrate of claim 5, wherein each $R_9$ and $R_{12}$ is chlorine.

7. The GUD substrate of claim 6, wherein each $R_1$–$R_8$, $R_{10}$, and $R_{11}$ is hydrogen and $M^+$ is sodium.

8. A method of synthesizing a GUD substrate, comprising the steps of:

(a) forming a conjugate (III), having a formula:

wherein $R_1$, $R_2$, and $R_7$–$R_{12}$ are independently selected from the group consisting of:
hydrogen, fluorine, chlorine, bromine, iodine, alkyl, hydroxyl, alkoxy, carboxyl and nitro groups;

R$_3$–R$_6$ are independently selected from the group consisting of hydrogen, fluorine, chlorine, bromine, iodine, nitro and amino;

M$^+$ is selected from the group consisting of: proton, lithium, sodium, potassium, magnesium, calcium, barium, and ammonium ion;

Ac is an acetyl group; and

Me is a methyl group; and (b) replacing Ac and Me groups with hydrogens.

9. The method of claim 8, wherein each R$_9$ and R$_{12}$ is chlorine.

10. The method of claim 8, wherein each R$_1$–R$_8$, R$_{10}$, and R$_{11}$ is hydrogen and M$^+$ is sodium.

11. The method of claim 10, wherein the step of forming the conjugate (III) comprises:

(a) mixing bromo-2,3,4-tri-O-acetyl-α-D-glucuronic acid methyl ester and a phenolsulphonphthalein to form a reaction mixture; and (b) maintaining the reaction mixture under conditions that allow the formation of the conjugate (III).

12. The method of claim 11, wherein the step of mixing further comprises adding a solution of potassium carbonate in N,N-dimethylformamide.

13. The method of claim 12, wherein the reaction mixture is stirred at room temperature.

14. The method of claim 12, further comprising a step of purifying the conjugate (III) by column chromatography on a silica gel.

15. The method of claim 13, wherein phenolsulphonphthalein is chlorophenol red.

16. The method of claim 10, wherein the step of replacing each Ac and Me groups with a hydrogen comprises:

(a) adding sulfuric acid to the conjugate (III) to form a second reaction mixture; and (b) maintaining the second reaction mixture under conditions that allow the replacement of Ac and Me groups with hydrogens.

17. The method of claim 16, wherein the second reaction mixture is stirred at room temperature.

18. A method for determining the presence of GUD activity in a sample comprising the steps of:

(a) contacting the sample with a GUD substrate having a formula:

wherein

R$_1$, R$_2$, and R$_7$–R$_{12}$ are independently selected from the group consisting of:

hydrogen, fluorine, chlorine, bromine, iodine, alkyl, hydroxyl, alkoxy, carboxyl and nitro groups;

R$_3$–R$_6$ are independently selected from the group consisting of hydrogen, fluorine, chlorine, bromine, iodine, nitro and amino;

M$^+$ is selected from the group consisting of: proton, lithium, sodium, potassium, magnesium, calcium, barium, and ammonium ion; and the sample and the GUD substrate are contacted under a condition that allows release of phenolsulphonphthalein;

(b) detecting phenolsulphonphthalein in the sample; and (c) correlating the presence of phenolsulphonphthalein in the sample to a presence of GUD.

19. The method of claim 18, wherein the detection step is carried out by measuring light absorption of the sample within a wavelength range that includes a wavelength of maximum absorption by phenolsulphonphthalein.

20. The method of claim 19, further comprising a step of correlating the intensity of the measured light absorption to the activity of GUD in the test sample.

21. The method of claim 19, further comprising a step of correlating the intensity of the measured light absorption to the concentration of GUD in the test sample.

22. The method of claim 19, wherein the phenolsulphonphthalein is chlorophenol red.

23. The method of claim 22, wherein the wavelength range is from 500 nm to 600 nm.

24. A test kit for determining the presence of GUD in a test sample, said test kit comprising a compound of the formula:

wherein

R$_1$, R$_2$, and R$_7$–R$_{12}$ are independently selected from the group consisting of:

hydrogen, fluorine, chlorine, bromine, iodine, alkyl, hydroxyl, alkoxy, carboxyl and nitro groups;

R$_3$–R$_6$ are independently selected from the group consisting of hydrogen, fluorine, chlorine, bromine, iodine, nitro and amino; and M$^+$ is selected from the group consisting of: proton, lithium, sodium, potassium, magnesium, calcium, barium, and ammonium ion.

* * * * *